United States Patent [19]

Hörner

[11] Patent Number: 5,115,005

[45] Date of Patent: May 19, 1992

[54] PHOSPHINIC ACID FLAME RETARDANTS

[75] Inventor: Hans-Peter Hörner, Wehr, Fed. Rep. of Germany

[73] Assignee: Ciba-Geigy Corporation, Ardsley, N.Y.

[21] Appl. No.: 756,405

[22] Filed: Sep. 9, 1991

[30] Foreign Application Priority Data

Sep. 12, 1990 [CH] Switzerland ............... 2950/90

[51] Int. Cl.$^5$ .................. C07F 9/32; C08K 5/5313
[52] U.S. Cl. ..................... 524/133; 523/451; 524/135; 558/108; 558/179; 558/182
[58] Field of Search .............. 558/108, 179, 182; 524/133, 135; 523/451

[56] References Cited

U.S. PATENT DOCUMENTS 4,178,399 12/1979 Hall et al. .................. 558/179

Primary Examiner—Veronica P. Hoke
Attorney, Agent, or Firm—JoAnn Villamizar

[57] ABSTRACT

Compounds of the formula Ia or Ib

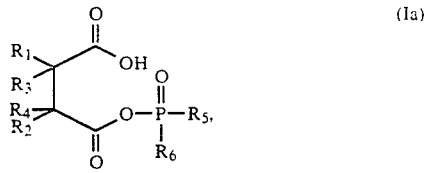

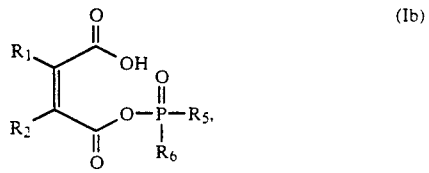

in which $R_1$ and $R_2$, independently of one another, are hydrogen, alkyl, cycloalkyl, alkenyl, aryl or aralkyl or, together with the carbon atoms in the α-position to the carbonyl groups, form a cyclopentane, cyclopentene, cyclohexane, cyclohexene, cyclohexadiene or bicyclo[2.2.1]hept-5-ene ring which is unsubstituted or substituted by $C_1$–$C_4$alkyl, or form a monocyclic or polycyclic, aromatic ring system which is unsubstituted or substituted by $C_1$–$C_4$alkyl, $R_3$ and $R_4$, independently of one another, are hydrogen, alkyl, alkenyl, aryl or aralkyl, and $R_5$ and $R_6$, independently of one another, are alkyl, aryl or aralkyl groups, are highly suitable as flame retardants for polymers.

12 Claims, No Drawings

PHOSPHINIC ACID FLAME RETARDANTS

The present invention relates to novel phosphorus compounds, to polymers containing these phosphorus compounds, and to the use of the phosphorus compounds as flame retardants for polymers.

The flame resistance of polymers is generally improved by reducing the organic content, for example by adding noncombustible or low-combustibility fillers, for example quartz sand, glass, wollastonite, etc. However, the filler content must be high to achieve adequate flameproofing, which can result in insolvable problems in the preparation and processing of the reactive resin compositions.

Another possibility is to add flameproofing agents to the polymers. Suitable compounds are inorganic additives, for example boron compounds or metal hydroxides. Here again, high contents of such additives are necessary, which likewise has an adverse effect on the preparation and processing.

The use of halogenated compounds, such as tetrabromobisphenol A, decabromodiphenyl ether or highly brominated polystyrenes, is controversial since disposal of polymers containing these compounds is questionable for ecological reasons. Combustion has the potential danger of the formation of highly toxic (dioxin-like) products.

U.S. Pat. No. 3,689,602 discloses halogenated phosphoric acid esters as flame-retardant additives for plastics. U.S. Pat. No. 4,220,472 describes dioxaphosphinane oxides as flameproofing agents for polymers, in particular for cellulose.

The use of organophosphorus compounds which are not incorporated into the polymers for flameproofing causes a plasticiser effect, which results in frequently severe impairment of the mechanical and electrical properties of the polymers. Thus, for example, the strength values or the glass transition temperature are reduced due to the plasticising effect of the organophosphorus compound. In addition, these compounds are usually unstable to hydrolysis, which results in undesired absorption of water by the cured resin with simultaneous formation of various phosphoric acid compounds.

It has now been found, suprisingly, that addition of acid esters made from phosphinic acids and dicarboxylic anhydrides allows unfilled, halogen-free resins having self-extinguishing properties to be prepared.

The present invention relates to compounds of the general formula Ia or Ib

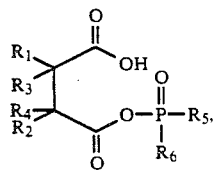
(Ia)

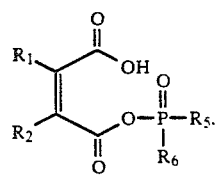
(Ib)

in which $R_1$ and $R_2$, independently of one another, are hydrogen, alkyl, cycloalkyl, alkenyl, aryl or aralkyl or, together with the carbon atoms in the α-position to the carbonyl groups, form a cyclopentane, cyclopentene, cyclohexane, cyclohexene, cyclohexadiene or bicyclo[2.2.1]hept-5-ene ring which is unsubstituted or substituted by $C_1$–$C_4$alkyl, or form a monocyclic or polycyclic, aromatic ring system which is unsubstituted or substituted by $C_1$–$C_4$alkyl, $R_3$ and $R_4$, independently of one another, are hydrogen, alkyl, alkenyl, aryl or aralkyl, and $R_5$ and $R_6$, independently of one another, are alkyl, aryl or aralkyl groups.

Rings formed by $R_1$ and $R_2$ may be monosubstituted or polysubstituted by $C_1$–$C_4$alkyl, in particular ethyl and especially methyl. Preference is given to two, in particular one, $C_1$–$C_4$alkyl substituent.

If any substituents are alkyl, cycloalkyl or alkenyl, they may be linear or branched alkyl having 1 to 20, preferably 1 to 6, particularly preferably 1 to 4, carbon atoms, cycloalkyl having 5 to 8, in particular 5 or 6, ring carbon atoms or linear or branched alkenyl having 2 to 12, in particular 2 to 6, carbon atoms. Aryl substituents are $C_1$–$C_4$alkyl-substituted or unsubstituted aromatic groups having 6 to 14 ring carbon atoms. Aralkyl groups may contain 7 to 12 carbon atoms, with benzyl being preferred.

Examples of radicals $R_1$ to $R_6$ as defined are: methyl, ethyl, propyl, isopropyl, n-butyl, i-butyl, t-butyl, pentyl, hexyl, octyl, dodecyl, tetradecyl, eicosyl, cyclopentyl, cyclohexyl, methylcyclohexyl, vinyl, prop-1-enyl, prop-2-enyl, n-but-3-enyl, n-pent-4-enyl, n-hex-5-enyl, phenyl, naphthyl, biphenyl, benzyl, methylbenzyl and phenylethyl.

The substituents $R_5$ and $R_6$ are preferably $C_1$–$C_6$alkyl groups; $R_5$ is particularly preferably ethyl and $R_6$ is particularly preferably methyl.

Preference is given to compounds of the formula Ia or Ib in which $R_1$, $R_2$, $R_3$ and $R_4$ are each hydrogen.

Preference is furthermore given to compounds of the formula Ia or Ib in which $R_1$ and $R_2$, together with the carbon atoms in the α-position to the carbonyl groups, form a $C_1$–$C_4$alkyl-substituted or unsubstituted cyclohexane, cyclohexene, cyclohexadiene, bicyclo[2.2.1]hept-5-ene or benzene ring.

Particular preference is given to compounds of the formula II

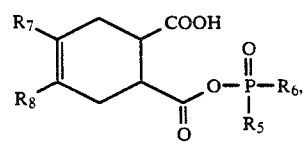
(II)

in which $R_7$ and $R_8$, independently of one another, are hydrogen or $C_1$–$C_4$alkyl, and $R_5$ and $R_6$ are as defined above.

Particular preference is given to the compound of the formula II in which $R_7$ is a methyl group, $R_8$ is hydrogen, $R_5$ is ethyl and $R_6$ is methyl.

The compounds according to the invention can be prepared by reacting, for example, a dicarboxylic anhydride of the formula IIIa or IIIb

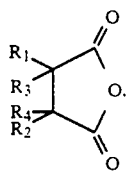

(IIIa)

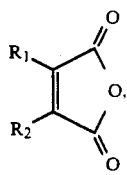

(IIIb)

in which the radicals $R_1$, $R_2$, $R_3$ and $R_4$ are as defined above, in approximately equimolar amounts with a phosphinic acid of the formula IV

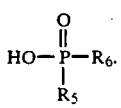

(IV)

in which $R_5$ and $R_6$ are as defined above, at elevated temperature.

The dicarboxylic anhydrides of the formulae IIIa and IIIb are known and are commercially available or can be prepared by known methods.

Specific examples of preferred compounds of the formula IIIa or IIIb are: succinic anhydride, dodecylsuccinic anhydride, tetramethylsuccinic anhydride, maleic anhydride, methylmaleic anhydride, diphenylmaleic anhydride, phthalic anhydride, tetrahydrophthalic anhydride, methyltetrahydrophthalic anhydride, hexahydrophthalic anhydride, methylhexahydrophthalic anhydride, bicyclo[2.2.1]hept-5-ene-2,3-dicarboxylic anhydride (nadic anhydride), methylbicyclo[2.2.1]hept-5-ene-2,3-dicarboxylic anhydride (methylnadic anhydride) and naphthalene-1,8-dicarboxylic anhydride.

Particularly preferred anhydrides are dodecylsuccinic anhydride, methylnadic anhydride, hexahydrophthalic anhydride, methylhexahydrophthalic anhydride and in particular methyltetrahydrophthalic anhydride.

The phosphinic acids of the formula IV are also known (see, for example, Houben-Weyl, "Methoden der Organischen Chemie" [Methods of Organic Chemistry], Volume XII/1, pp. 220-240 (1963) and Volume E2, pp. 123-148 (1982)), and some are commercially available.

Examples of compounds of the formula IV are: dimethylphosphinic acid, ethylmethylphosphinic acid, diethylphosphinic acid, n-propylmethylphosphinic acid, n-propylethylphosphinic acid, di-n-propylphosphinic acid, diisopropylphosphinic acid and diphenylphosphinic acid.

The compounds of the formula Ia or Ib are suitable, for example, as flame-retardant substances for polymers, in particular for epoxy resins.

The present invention therefore also relates to compositions comprising a polymer and at least one compound of the formula Ia or Ib.

The amount of the compounds of the formula Ia or Ib to be added to the polymers as flame retardants may vary within broad limits. In general, the compositions according to the invention contain from 1 to 50% by weight, preferably from 5 to 40% by weight and particularly preferably from 15 to 25% by weight, of a compound of the formula Ia or Ib. The optimum amount depends on the nature of the polymer and on the type of compound of the formulae Ia and Ib employed and can easily be determined experimentally.

Since the compounds of the formulae Ia and Ib are generally effective even when added in small amounts and are in addition halogen-free, they cause fewer undesired effects in the polymer than other known flame retardants.

Depending on the type of polymer used and on the desired properties, the compounds of the formula Ia or Ib can be used in various physical forms. Thus, they can be ground to give a finely divided form, for example in order to achieve better dispersion in the polymer. If desired, it is also possible to employ mixtures of various compounds of the formula Ia or Ib.

The compounds of the formula Ia or Ib can be used in various polymers. Suitable polymers which can be flameproofed therewith are, for example:

1. Polyphenylene oxides and sulfides and mixtures of these polymers with polystyrene graft polymers or styrene copolymers, for example high-impact polystyrene, and EPDM copolymers with rubbers, and mixtures of polyphenylene oxides with polyamides and polyesters.

2. Polyurethanes derived on the one hand from polyethers, polyesters or polybutadiene containing terminal hydroxyl groups and on the other hand from aliphatic or aromatic polyisocyanates, including polyisocyanurates and precursors thereof.

3. Polyamides and copolyamides derived from diamines and dicarboxylic acids and/or from aminocarboxylic acids or the corresponding lactams, such as nylon 4, nylon 6, nylon 6/6, nylon 6/10, nylon 11, nylon 12, poly-2,4,4-trimethylhexamethylene terephthalamide or poly-m-phenylene isophthalamide, and copolymers thereof with polyethers, for example with polyethylene glycols, polypropylene glycols or polytetramethylene glycols.

4. Polyesters derived from dicarboxylic acids and dialcohols and/or hydroxycarboxylic acids or the corresponding lactones, for example polyethylene terephthalate, polybutylene terephthalate, poly-1,4-dimethylolcyclohexane terephthalate and polyhydroxybenzoates, and block copolyether-esters derived from polyethers containing terminal hydroxyl groups.

5. Unsaturated polyesters derived from copolyesters of saturated and unsaturated dicarboxylic acids and polyhydric alcohols and vinyl compounds as crosslinking agents.

6. Polystyrene.

7. Graft copolymers of styrene, for example styrene on polybutadiene, styrene and acrylonitrile on polybutadiene, styrene and alkyl acrylates or methacrylates on polybutadiene, styrene and acrylonitrile on ethylene-propylene-diene terpolymers, styrene and acrylonitrile on acrylate-butadiene copolymers, and mixtures thereof with random copolymers of styrene or $\alpha$-methylstyrene and dienes or acrylic acid derivatives, for example the styrene terpolymers known as ABS, MBS, ASA or AES.

8. Epoxy resins derived from polyepoxides, for example from bisdiglycidyl ethers, in particular bisphenol A diglycidyl ethers, or from cycloaliphatic diepoxides.

9. Polycarbonates.

The compounds of the formula Ia or Ib are particularly suitable for flameproofing epoxy resins, for example bisphenol A resins, bisphenol F resins, phenol-and cresol-novolak epoxy resins, which are cured using carboxylic anhydrides, for example phthalic anhydride, hexahydrophthalic anhydride, methyltetrahydrophthalic anhydride, methylhexahydrophthalic anhydride or methylnadic anhydride.

The advantage in this application is that the phosphorus compound of the formula Ia or Ib is admixed with the anhydride curing agent and incorporated reactively into the polymer structure. In this way, a cured resin having self-extinguishing properties is obtained without other flame-retardant substances being added.

The curing agent mixtures preferably comprise 10–60% by weight, in particular 30–50% by weight, of an acidic ester of the formula Ia or Ib and 90–40% by weight, in particular 70–50% by weight, of a dicarboxylic anhydride.

The unfilled and halogen-free, epoxy resin-based reactive resin compositions according to the invention can be employed, for example, as casting and laminating resins and in the area of electronics encapsulation systems.

The compositions according to the invention may also contain other conventional additives, for example thermal stabilisers, light stabilisers, UV absorbers, antioxidants, antistatics, preservatives, adhesion promoters, fillers, pigments, lubricants, foaming agents, fungicides, plasticisers, processing assistants, further flame-retardant additives and agents for reducing the evolution of smoke.

Additional flame retardants which can be employed together with the compounds of the formula Ia or Ib used according to the invention are, for example, phosphorus-containing salts, for example ammonium polyphosphates, antimony trioxide, aluminium hydroxide, bismuth oxide, molybdenum oxide or mixtures of these compounds with oxides or salts of zinc and/or magnesium.

The invention is described in greater detail by means of the examples below.

PREPARATION EXAMPLE

Example 1: Acidic ester made from 4-methylcyclohex-4-enedicarboxylic anhydride and ethylmethylphosphinic acid 166 g (1 mol) of 4-methylcyclohex-4-enedicarboxylic anhydride are mixed with 108 g (1 mol) of ethylmethylphosphinic acid, and the mixture is stirred vigorously for 4 hours at 100° C. under a nitrogen atmosphere. The acidic ester is subsequently removed from the reaction mixture by vacuum distillation (b.p.=180° C./0.001 mmHg). Yield 214.5 g (80%).

USE EXAMPLES

EXAMPLES A-C

The acidic ester prepared as described in Example 1 is mixed in three different ratios with 4-methylcyclohex-4-ene-1,2-dicarboxylic anhydride. The compositions of the curing agent mixtures obtained in this way are shown in Table 1.

TABLE 1

| Curing agent mixture | A | B | C |
|---|---|---|---|
| 4-Methylcyclohex-4-ene-1,2-dicarboxylic anhydride | 70 | 60 | 50 |

TABLE 1-continued

| Curing agent mixture | A | B | C |
|---|---|---|---|
| Acidic ester from Example 1 (% by weight) | 30 | 40 | 50 |

Curing agent mixtures A, B and C are reacted in the ratio 1:1 with an epoxy resin based on bisphenol A having an epoxide group content of 5.25–5.40 eq/kg. In order to increase the reactivity, 2% by weight of n-benzyldimethylamine are added as accelerator. The mixtures are cured for 1 hour at 80° C. and subsequently for 3 hours at 120° C. The cured resins obtained in this way are tested for their flame-retardant action in accordance with Underwriters Laboratories Inc. UL 94 standard, third revision of 25 September 1981 (horizontal combustibility test).

In addition, various mechanical and dielectric properties of the cured resins are measured. The results are summarised in Table 2.

TABLE 2

| Cured resin | A | B | C |
|---|---|---|---|
| Phosphorus content (% by weight) | 1.78 | 2.38 | 2.97 |
| Glass transition temperature $T_g$ (°C.) | 99 | 95 | 93 |
| Flame retardency accordance with UL 94 | | | |
| using 6 mm plates | V-1 | V-0 | V-0 |
| using 4 mm plates | V-1 | V-0 | V-0 |
| using 2 mm plates | n.c.* | V-1 | V-0 |
| Flexural impact strength (kJ/m$^2$) | 11.7 | 9.3 | 5.1 |
| Flexural strength (N/mm$^2$) | 121 | 98 | 78 |
| Modulus of elasticity (N/mm$^2$) | 4220 | 4105 | 3360 |
| Tensile strength (N/mm$^2$) | 78.5 | 66.5 | 43.5 |
| Compressive strength (N/mm$^2$) | 140 | 136 | 100 |
| Relative dielectric constant $\epsilon_r$ | | | |
| at 23° C. | 3.35 | 3.42 | 3.39 |
| at 50° C. | 3.33 | 3.38 | 3.45 |
| at 100° C. | 4.28 | 4.78 | 5.25 |
| Dielectric loss factor tan δ | | | |
| at 23° C. | 0.0032 | 0.0032 | 0.0032 |
| at 50° C. | 0.0028 | 0.0028 | 0.0026 |
| at 100° C. | 0.0715 | 0.121 | 0.185 |

*n.c.: not classified

What is claimed is:

1. A compound of the formula Ia or Ib

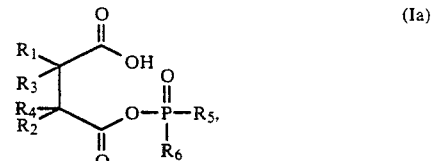

(Ia)

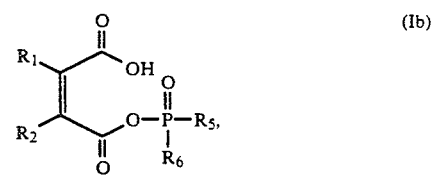

(Ib)

in which $R_1$ and $R_2$, independently of one another, are hydrogen, alkyl, cycloalkyl, alkenyl, aryl or aralkyl or, together with the carbon atoms in the α-position to the carbonyl groups, form a cyclopentane, cyclopentene, cyclohexane, cyclohexene, cyclohexadiene or bicyclo[2.2.1]hept-5-ene ring which is unsubstituted or substituted by $C_1$–$C_4$alkyl, or form a monocyclic or polycyclic, aromatic ring system which is unsubstituted or substituted by $C_1$-$C_4$alkyl, $R_3$ and $R_4$, independently of one another, are hydrogen, alkyl, alkenyl, aryl or aralkyl, and $R_5$ and $R_6$, independently of one another, are alkyl, aryl or aralkyl groups.

2. A compound of the formula Ia or Ib according to claim 1, in which $R_5$ and $R_6$ are $C_1$-$C_6$alkyl groups.

3. A compound of the formula Ia or Ib according to claim 2, in which $R_5$ is ethyl and $R_6$ is methyl.

4. A compound of the formula Ia or Ib according to claim 1, in which $R_1$, $R_2$, $R_3$ and $R_4$ are each hydrogen.

5. A compound of the formula Ia or Ib according to claim 1, in which $R_1$ and $R_2$, together with the carbon atoms in the $\alpha$-position to the carbonyl groups, form a $C_1$-$C_4$alkyl-substituted or unsubstituted cyclohexane, cyclohexene, cyclohexadiene, bicyclo[2.2.1]hept-5-ene or benzene ring.

6. A compound of the formula II according to claim 1

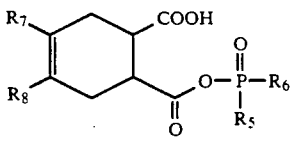
(II)

in which $R_7$ and $R_8$, independently of one another, are hydrogen or $C_1$-$C_4$alkyl, and $R_5$ and $R_6$ are as defined in claim 1.

7. A compound according to claim 6, in which $R_7$ is a methyl group, $R_8$ is hydrogen, $R_5$ is ethyl and $R_6$ is methyl.

8. A process for the preparation of a compound of the formula Ia or Ib according to claim 1, wherein a dicarboxylic anhydride of the formula IIIa or IIIb

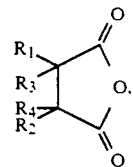
(IIIa)

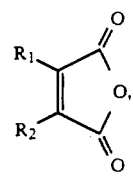
(IIIb)

in which the radicals $R_1$, $R_2$, $R_3$ and $R_4$ are as defined in claim 1, is reacted in approximately equimolar amounts with a phosphinic acid of the formula IV

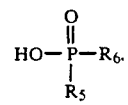
(IV)

in which $R_5$ and $R_6$ are as defined in claim 1, at elevated temperature.

9. A composition comprising a polymer and a flame retardant amount of at least one compound of the formula Ia or Ib according to claim 1.

10. A composition according to claim 9, containing from 1 to 50% by weight of a compound of the formula Ia or Ib.

11. A composition according to claim 9, containing an epoxy resin.

12. A composition according to claim 11, containing, as curing agent, a mixture of from 40 to 90% by weight of a dicarboxylic anhydride and from 60 to 10% by weight of a compound of the formula Ia or Ib.

* * * * *